US006534964B1

(12) United States Patent
Sinha (10) Patent No.: US 6,534,964 B1
(45) Date of Patent: Mar. 18, 2003

(54) APPARATUS AND METHOD FOR DETERMINING STIFFNESS PROPERTIES OF AN ANISOTROPIC ELECTRONIC SUBSTRATE USING SCANNING ACOUSTIC MICROSCOPY

(75) Inventor: Arvind K. Sinha, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 1 day.

(21) Appl. No.: 09/668,782

(22) Filed: Sep. 22, 2000

(51) Int. Cl.[7] .............................................. G01N 27/00
(52) U.S. Cl. ...................................... 324/71.1; 73/597
(58) Field of Search ............................... 324/71.1, 500, 324/537, 532, 535, 764, 765; 73/596, 601, 597, 598; 379/406–411

(56) References Cited

U.S. PATENT DOCUMENTS

| | | | | |
|---|---|---|---|---|
| 3,858,437 A | * | 1/1975 | Jarzynski et al. ............. 73/67.5 |
| 4,106,327 A | * | 8/1978 | Adler et al. ...................... 73/1 |
| 4,631,964 A | * | 12/1986 | Sprunt et al. .................. 73/594 |
| 5,115,673 A | * | 5/1992 | Kline et al. .................... 73/601 |
| 5,154,081 A | * | 10/1992 | Thompson et al. ............ 73/597 |
| 5,408,882 A | * | 4/1995 | McKinley et al. ............. 73/597 |
| 5,433,112 A | * | 7/1995 | Piche et al. .................... 73/597 |
| 5,714,688 A | * | 2/1998 | Buttram et al. ................ 73/597 |
| 5,824,908 A | * | 10/1998 | Schindel et al. ............... 73/632 |
| 6,047,600 A | * | 4/2000 | Ottosson et al. .............. 73/597 |
| 6,061,444 A | * | 5/2000 | Kawahara et al. .......... 379/410 |

* cited by examiner

Primary Examiner—N. Le
Assistant Examiner—Amy He
(74) Attorney, Agent, or Firm—Martin & Associates, LLC; Derek P. Martin (57) ABSTRACT

An apparatus and method allow accurately determining properties of an anisotropic material, such as a multilayer printed wiring board, in a non-destructive manner using scanning acoustic microscopy. The apparatus and method includes special signal processing that allows determining the time of flight of an input waveform from a transmitter transducer on one side of the printed wiring board to a receiver transducer positioned on the opposite side of the printed wiring board in a position that opposes the transmitter transducer. The special signal processing includes an auto-correlation function and a cepstrum analysis. Once the time of flight is determined, the velocity of the input waveform may be computed. The Young's modulus and shear modulus for the printed wiring board may then be computed from the velocity of the input waveform. The preferred embodiments allow determining properties of a printed wiring board without the necessity of destructive testing.

14 Claims, 6 Drawing Sheets

FIG. 1

Prior Art

APPARATUS AND METHOD FOR DETERMINING STIFFNESS PROPERTIES OF AN ANISOTROPIC ELECTRONIC SUBSTRATE USING SCANNING ACOUSTIC MICROSCOPY

BACKGROUND OF THE INVENTION

1. Technical Field

This invention generally relates to test equipment and more specifically relates to equipment for testing properties of materials.

2. Background Art

Electronics have become essential to our modern way of life in the United States. Electronic assemblies are typically made by installing individual components into a printed wiring board (PWB), which are then soldered into place. The PWB makes all the connections between electronic and electrical components using metal paths that are typically etched into the PWB. Modern PWBs have become very sophisticated and complex, and it is not uncommon to have a PWB today that has in excess of twenty layers. Each layer defines conductor paths that connect to one or more other layers. The many different layers allow packing the components very tightly onto a PWB, thereby reducing the overall area of the PWB. This minimization in size of an electronic assembly is essential for many applications where the size of the electronic assembly must be kept very small, as in mobile phones and other hand-held electronic devices.

As the number of layers in printed wiring boards increases, the physical properties of the boards becomes more and more difficult to estimate. Because each layer can include many areas of metal and many areas without metal, the resulting printed wiring board has features that are asymmetrically distributed. Due to the anisotropic nature of these complex printed wiring boards, destructive testing methods have been used to determine their material properties. However, some modem printed wiring boards are sufficiently complex that they are very expensive, with a cost of thousands of dollars for a bare board. Needless to say, spending these high sums of money to perform destructive testing is undesirable. Without a method for economically determining the properties of anisotropic materials such as printed wiring boards in a nondestructive manner, either these properties will be estimated rather than measured, or the cost of determining these properties using destructive testing will remain excessive.

DISCLOSURE OF INVENTION

According to the preferred embodiments, an apparatus and method allow accurately determining properties of an anisotropic material, such as a multilayer printed wiring board, in a non-destructive manner using scanning acoustic microscopy. The apparatus and method includes special signal processing that allows determining the time of flight of an input waveform from a transmitter transducer on one side of the printed wiring board to a receiver transducer positioned on the opposite side of the printed wiring board in a position that opposes the transmitter transducer. The special signal processing includes an auto-correlation function and a cepstrum analysis. Once the time of flight is determined, the velocity of the input waveform may be computed. The Young's modulus and shear modulus for the printed wiring board may then be computed from the velocity of the input waveform. The preferred embodiments allow determining properties of a printed wiring board without the necessity of destructive testing.

The foregoing and other features and advantages of the invention will be apparent from the following more particular description of preferred embodiments of the invention, as illustrated in the accompanying drawings.

BRIEF DESCRIPTION OF DRAWINGS

The preferred embodiments of the present invention will hereinafter be described in conjunction with the appended drawings, where like designations denote like elements, and.

BEST MODE FOR CARRYING OUT THE INVENTION

Overview

The wave propagation theory for determining material properties for isotropic materials, such as metal alloys, is well-established and has been experimentally verified. For example, one text that discussed wave propagation theory and techniques for isotropic materials is R. Truell et al., "Ultrasonic Methods in Solid State Physics", Academic Press, New York, Chapter 2 (1969).

Figure 1:
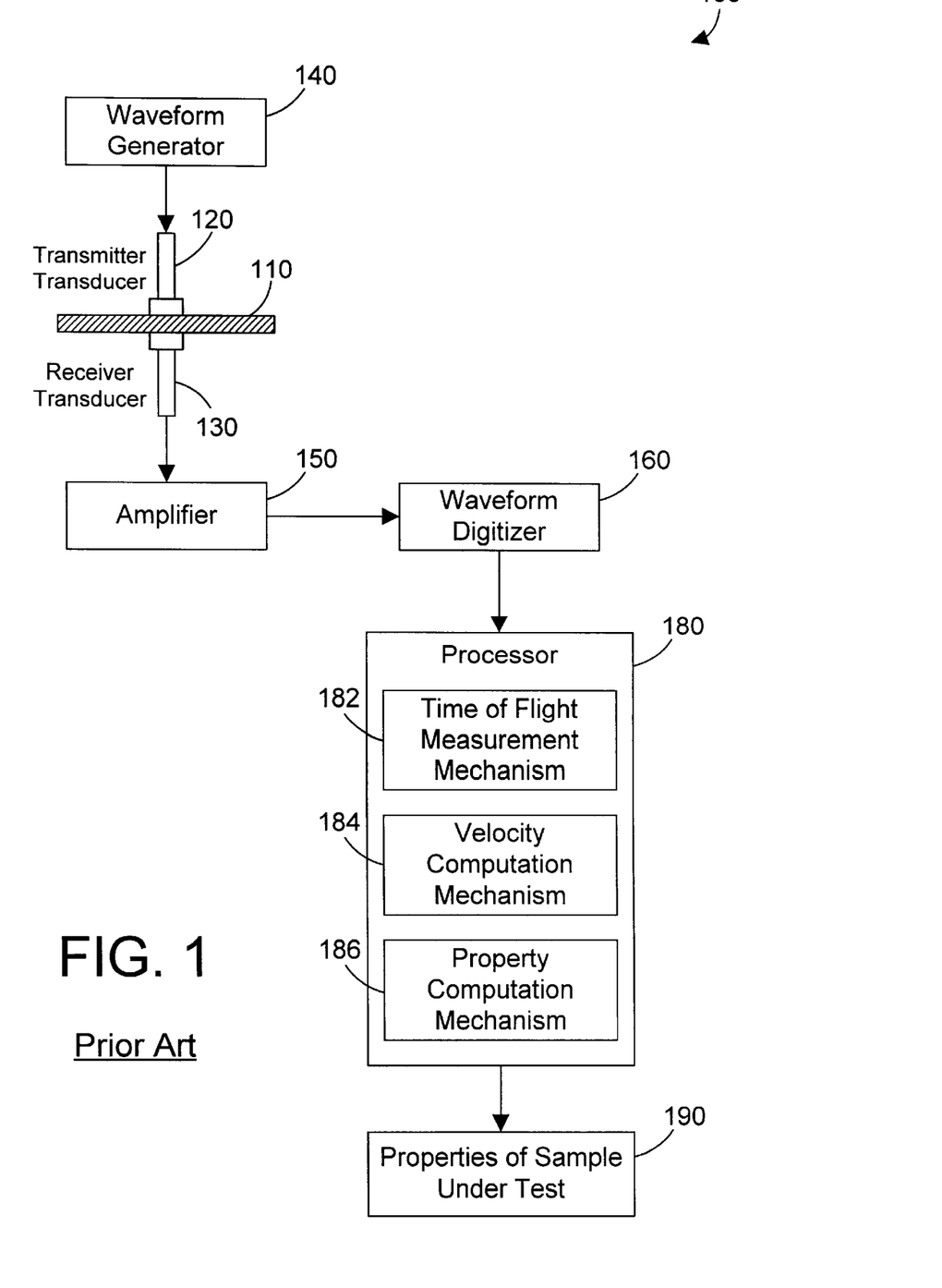
FIG. 1 is a block diagram of a prior art apparatus for determining properties of an isotropic material.

Referring to FIG. 1, a prior art apparatus 100 uses acoustic microscopy to determine properties of an isotropic sample under test 110. A transmitter transducer 120 is a piezoelectric element that is placed in contact with the sample under test 110. A waveform generator 140 is coupled to the transmitter transducer 120 to induce an input waveform onto the sample under test 110. A receiver transducer 130 is a piezoelectric element that is placed in contact with the opposite side of the sample under test 110, in a position that opposes the transmitter transducer 120. When waveform generator 140 impresses an input waveform on the transmitter transducer 120, the input waveform passes through the sample under test 110 and is detected by the receiver transducer 130. This signal is then amplified by amplifier 150. A waveform digitizer 160 then digitizes the amplified waveform received from amplifier 150.

The waveform digitizer outputs a digitized waveform to a processor 180. The processor 180 includes a time of flight measurement mechanism 182 that determines the time of flight from the digitized waveform received from the waveform digitizer 160. A velocity computation mechanism 184 is then used to compute the velocity that the input waveform traveled across the sample under test. The velocity is equal to the distance (i. e., thickness of the sample under test) divided by the time of flight received from the time of flight measurement mechanism 182. Once the velocity is determined, the stiffness modulus $C_{11}$ can be determined from the formula $$C_{11} = \rho v^2 \qquad (1)$$

Once $C_{11}$ has been determined, the Young's modulus E and shear modulus G can be computed from the following formulae:

$$E = \frac{(3GC_{11} - 4G^2)}{(C_{11} - G)} \quad (2)$$

$$G = \frac{E}{2(1 - C_{12}/C_{11})} \quad (3)$$

Figure 2:
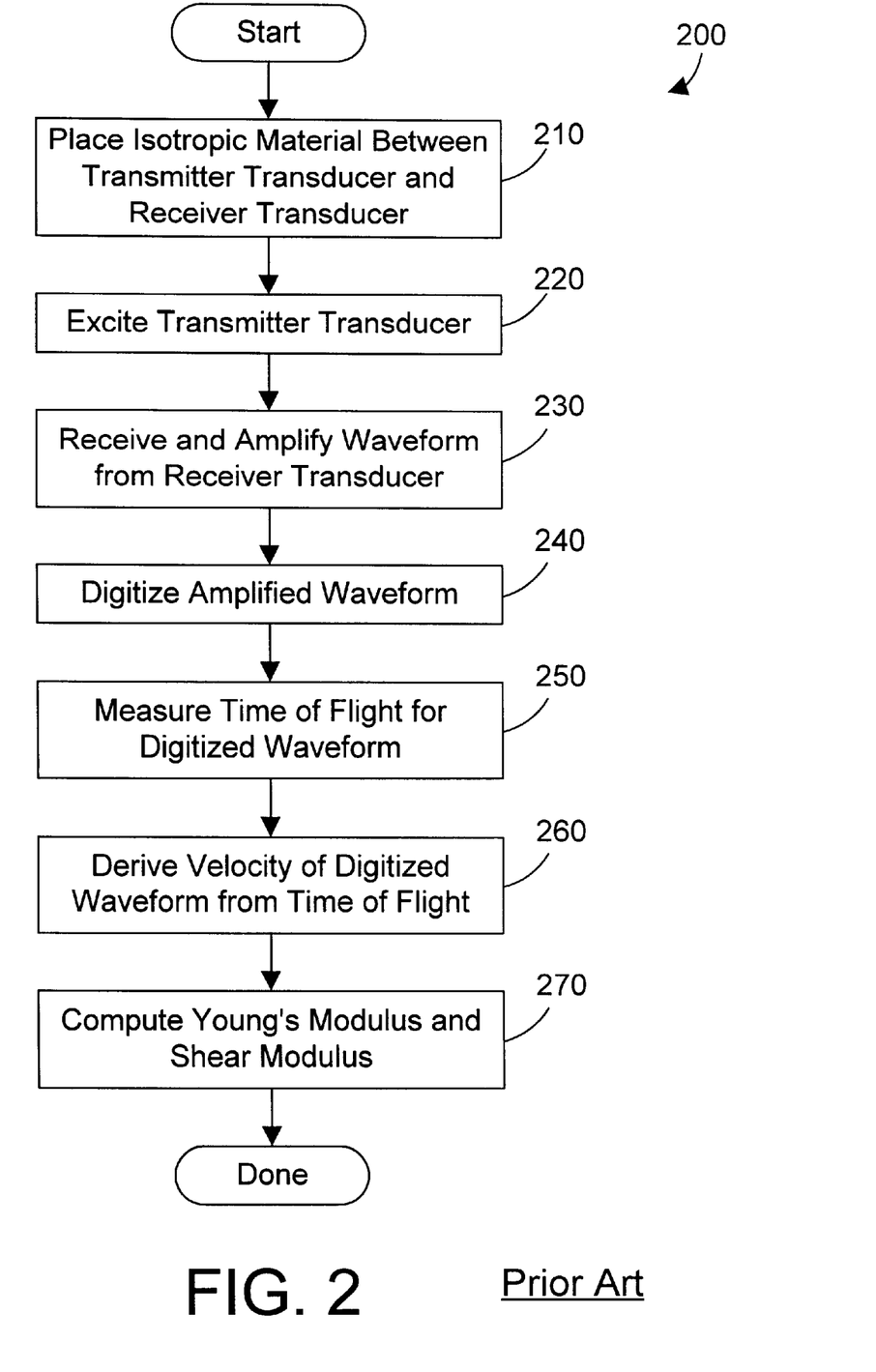
FIG. 2 is a flow diagram of a prior art method for testing properties of an isotropic material using the apparatus of FIG. 1.

Referring now to FIG. 2, a method 200 for determining properties of an isotropic material begins by placing the isotropic material (e.g., sample under test 110 in FIG. 1) between a transmitter transducer and receiver transducer (step 210), as shown in FIG. 1. Next, the transmitter transducer is excited with an input waveform (step 220). The receiver transducer receives the input waveform after it passes through the sample under test, and this waveform is then amplified (step 230). The amplified waveform is then digitized (step 240). The time of flight for the digitized waveform is then determined (step 250). The velocity of the digitized waveform is then determined from the time of flight (step 260). Once the velocity is known, the Young's modulus and shear modulus are then computed (step 270). These computed properties in step 270 may then be used to characterize the stiffness of the sample under test in computer models.

One known method for measuring properties of composite materials uses principles of ultrasonic interference spectroscopy, and is described in Chang et al., "Ultrasonic Resonance Measurement of Sound Velocity in Thin Composite Laminates", Journal of Composite Materials, Vol. 8, p. 356–363 (1974). Using the method of Chang et al., instead of applying a transmission time method, a frequency spectrum of the pulsed signal reflected from opposite surfaces of a thin specimen is obtained using a digitizing scheme and an analytical Fourier transform. Periods of anti-resonance dips in the frequency spectra were related to the velocity of sound and material thickness. The Chang et al. method works in the frequency domain, and uses a Fourier transform to detect the periods of anti-resonance dips in the frequency spectra referenced above.

Known methods for measuring properties in isotropic materials are generally not suitable for anisotropic materials, such as a printed wiring board. Other known methods of measuring properties in composite materials (e.g., Chang et al., above) are useful for some types of composite materials. However, these techniques have not been used to evaluate the properties of a multilayer electronic substrate, such as a printed wiring board. A multilayer printed wiring board is typically made of a number of power planes consisting of thin copper layers sandwiched in between layers of fiberglass and epoxy, commonly referred to in the art as FR4. The different layers on a printed wiring board that includes numerous layers greatly attenuate the strength and quality of an acoustic signal that attempts to pass through the sample under test when testing with a prior art apparatus and method as described above with reference to FIGS. 1 and 2. As a result, known techniques for evaluating properties of isotropic and composite materials are not suitable for use on a multilayer printed wiring board. The preferred embodiments herein disclose an apparatus and method for evaluating properties of a multilayer printed wiring board, which is simply one class of materials that are generically referred to herein as anisotropic materials.

DETAILED DESCRIPTION

The preferred embodiments relate to the determination of stiffness properties in an anisotropic material, such as a multilayer printed wiring board, using scanning acoustic microscopy. An acoustic waveform is introduced by a transmitter transducer to one side of the sample under test, while a receiver transducer on the opposite side of the sample under test receives the waveform after it propagates through the sample under test. The signal received by the receiver transducer is amplified, digitized, and processed by a digital signal processor to determine the time of flight of the waveform between the transmitter transducer and the receiver transducer. Once the time of flight is determined, the velocity can be derived, from which the Young's modulus and shear modulus can be determined for the sample under test.

The stiffness properties (or elastic properties) of a sample under test are expressed by the Young's modulus and shear modulus for the sample under test. In linear elasticity, the relationship between stress and strain is usually expressed in the form:

$$\{\sigma\}=[C]\{\epsilon\} \quad (4)$$

$$\sigma_{ij}=C_{ijkl}\epsilon_{ij} \text{ where } 1 \leq i,j,k,l \leq 3 \quad (5)$$

In the above equation the summation convention over the repeated indexes is used, and [C] is a 6×6 matrix whose elements are the elastic constants for the material. The relationship does not distinguish the tensile behavior from the compressive behavior of the sample under test, which means that the sample under test is assumed to have the same stiffness under tension and compression. The matrix of elastic constants [C] can be shown to be symmetric from the strain energy consideration. Thus, 21 independent elastic constants exist for the most anisotropic material. Here we assume that there exists three mutually orthogonal planes of material symmetry, thereby reducing the number of unknowns to 9. We have also assumed that the material has an axis of the symmetry, making this a transversely isotropic material. This reduces the unknown in the stiffness matrix to five independent properties. These assumptions may not hold for all materials, but they apply reasonably well to multilayer printed wiring boards, thereby reducing the number of experimental measurements. The stiffness matrix with the assumptions made above has the form shown in Table 1.

TABLE 1

| $C_{11}$ | $C_{12}$ | $C_{13}$ | 0 | 0 | 0 |
|---|---|---|---|---|---|
| $C_{12}$ | $C_{22}$ | $C_{23}$ | 0 | 0 | 0 |
| $C_{12}$ | $C_{23}$ | $C_{22}$ | 0 | 0 | 0 |
| 0 | 0 | 0 | $\frac{(C_{22} - C_{23})}{2}$ | 0 | 0 |
| 0 | 0 | 0 | 0 | $C_{66}$ | 0 |
| 0 | 0 | 0 | 0 | 0 | $C_{66}$ |

The independent elastic constants are $C_{11}$, $C_{12}$, $C_{13}$, $C_{22}$, $C_{23}$, and $C_{66}$. Some of these constants may be used in accordance with the preferred embodiments to determine the Young's modulus and shear modulus for a sample under test, as described in more detail below.

Figure 3:
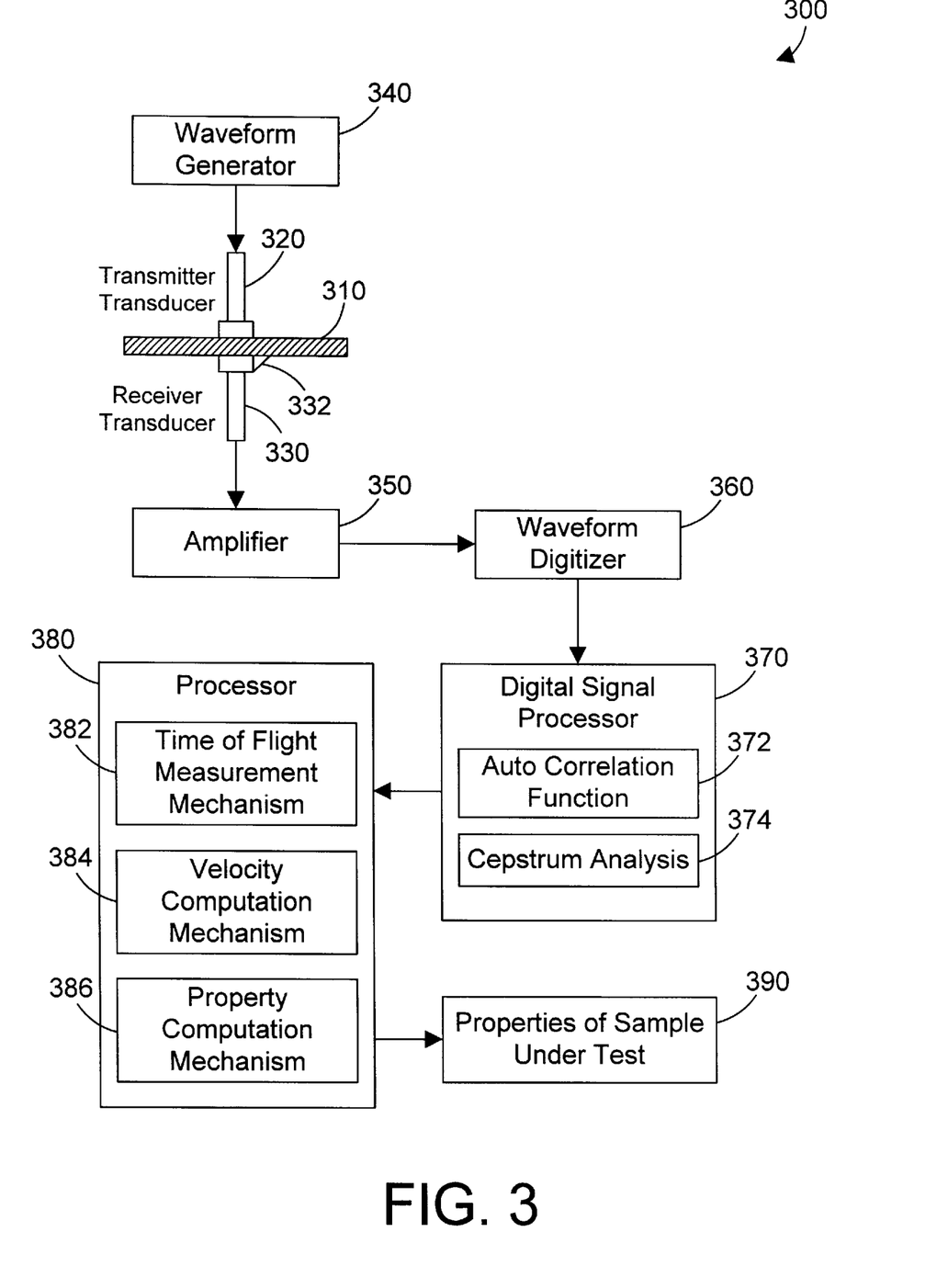
FIG. 3 is a block diagram of an apparatus for determining properties of an anisotropic material in accordance with the preferred embodiments.

Referring now to FIG. 3, an apparatus 300 in accordance with the preferred embodiments includes a transmitter transducer 320 and a receiver transducer 330 that are placed on opposing sides of an anisotropic sample under test 310, such as a multilayer printed wiring board. A waveform generator 340 excites the transmitter transducer 320 with an input waveform, thereby generating both longitudinal and shear waves in the sample under test 310. The longitudinal wave is generated directly by the transmitter transducer 320, while the shear wave is generated by placing an angled wedge 332 made of optically aligned translucent plastic adjacent to the receiver transducer 330. The receiver transducer 330 receives the input waveform after it has passed through the sample under test 310, which consists of both longitudinal and shear waves. This received waveform is then amplified by amplifier 350 to produce an amplified waveform. The waveform digitizer 360 then digitizes the amplified waveform received from amplifier 350.

The digitized waveform produced by waveform digitizer 360 does not readily provide the time of flight for the waveform through the sample under test if the sample under test is anisotropic, as is a multilayer printed wiring board. The various layers in a multilayer printed wiring board reduce the integrity of the waveform received by the receiver transducer 330, making it very difficult to tell which portions of the waveform correspond to the input waveform and which portions of the waveform correspond to noise introduced by the multiple layers in the sample under test. For this reason, special signal processing is required to extract the time of flight of the waveform through the sample under test. The waveform digitizer 360 thus outputs the digitized waveform to a digital signal processor 370. The digital signal processor 370 first performs an auto-correlation function 372, which gives a measure of the extent to which two similar signals correlate with each other as a function of time displacement between them. This requires that a second waveform at a different point in time be detected by the receiver transducer 330, amplified by the amplifier 350, and digitized by the waveform digitizer 360. At this point, the digital signal processor 370 has two waveforms separated in time, and the auto-correlation function is then performed on these two waveforms. The result is a new waveform that is much cleaner and devoid of white noise components. Next, the digital signal processor 370 performs a cepstrum analysis 374 of the new waveform produced by the auto-correlation function. A cepstrum analysis is a logarithmic conversion of the waveform. Once the cepstrum analysis is complete, the time of flight can be readily determined by the time of flight measurement mechanism 382 in processor 380. Once this time of flight is computed, the velocity of the input waveform passing through the sample under test may be computed by the velocity computation mechanism 384. Once velocity of the waveform is known, the property computation mechanism 386 can readily determine the Young's modulus and shear modulus for the sample under test.

Figure 4:
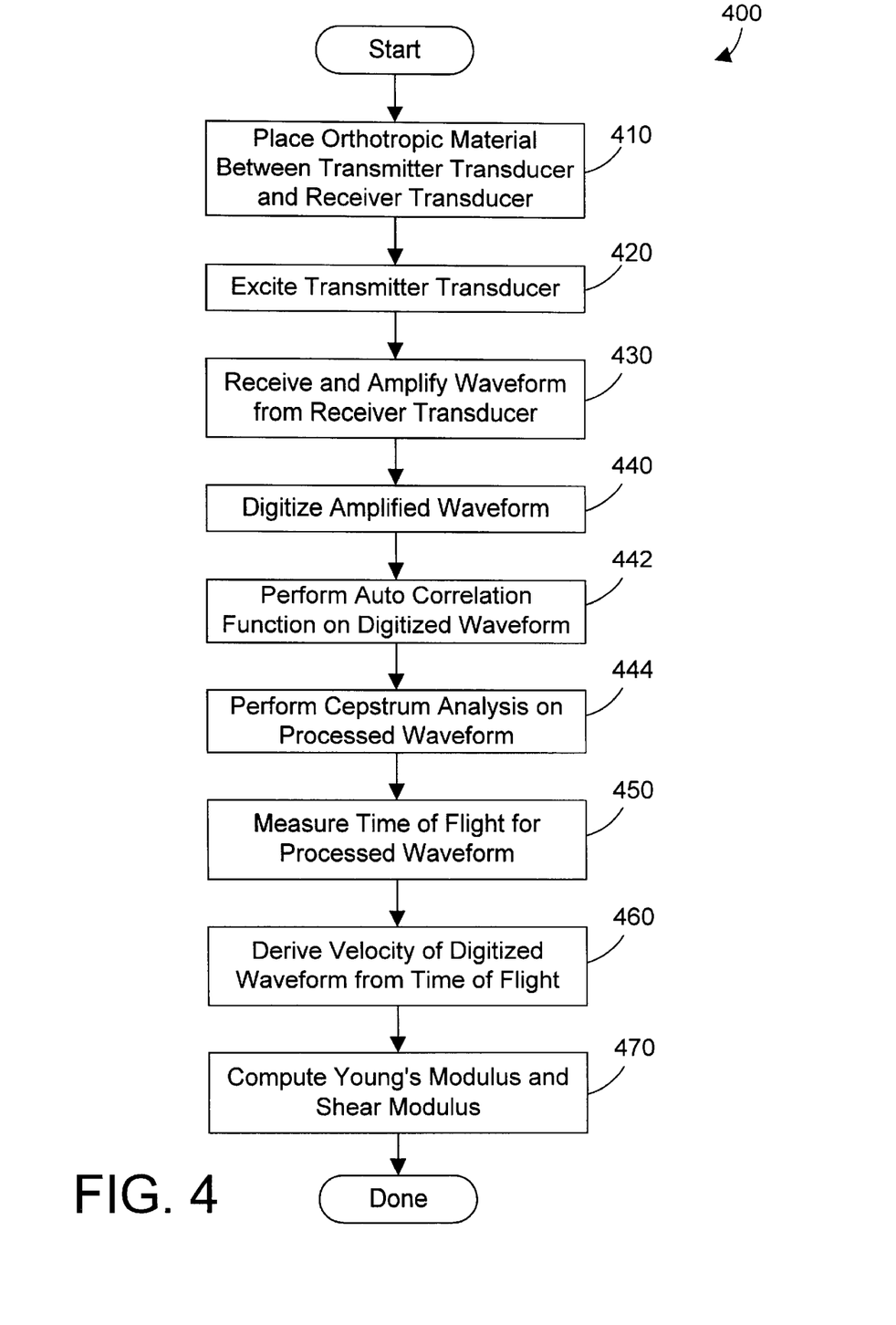
FIG. 4 is a flow diagram of a method in accordance with the preferred embodiments for determining properties of an anisotropic material.

Referring now to FIG. 4, a method 400 in accordance with the preferred embodiments determines stiffness properties of an anisotropic sample under test, such as a multilayer printed wiring board. Steps of method 400 correlate to features in the apparatus 300 of FIG. 3. First, the sample under test is placed between the transmitter transducer and the receiver transducer (step 410). The waveform generator then excites the transmitter transducer with an input waveform (step 420). The receiver transducer then receives the waveform after it passes through the sample under test, and the amplifier amplifies this waveform received by the receiver transducer (step 430). The amplified waveform is then digitized (step 440). An auto-correlation function is then performed on the digitized waveform (step 442), followed by a cepstrum analysis (step 444). The result is a waveform from which the time of flight may be readily determined (step 450). The time of flight is then used to compute the velocity of the input wave traveling through the sample under test (step 460). Finally, the velocity may be used to determine various stiffness properties of the sample under test, such as the Young's modulus and the shear modulus (step 470).

Test Results

Figure 5:
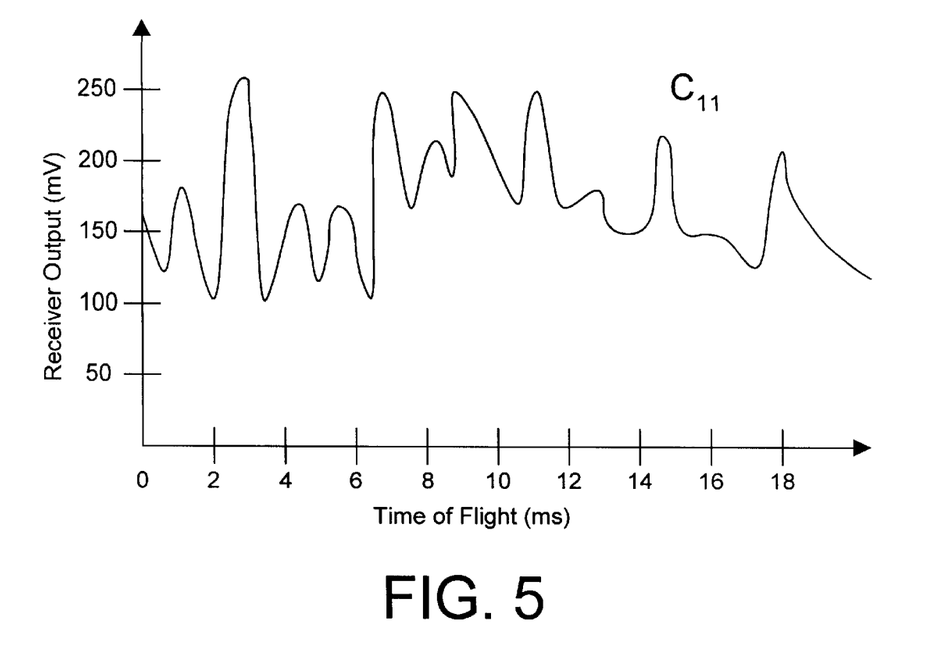
FIG. 5 is a graph showing a magnified, digitized waveform output by the waveform digitizer of FIG. 3.

The apparatus and method of the preferred embodiments were used to test various different materials, and the test results were then compared to results obtained by other methods of testing, such as destructive testing. The transmitter transducer was initially excited by the waveform generator with longitudinal and shear waves of sampling frequencies from 16 MHz to 120 MHz. The waveform received by the receiver transducer was amplified and digitized, and the resulting waveform is shown in FIG. 5. The time of flight of the input waveform cannot be readily determine from the waveform of FIG. 5. For this reason, the digitized waveform is then input into an auto-correlation function, $R_{aa}(t)$, which determines how two similar signals correlate with each other as a function of time displacement $t$ between them. For example, to apply the auto-correlation function, two signals (a) are collected, one at time t and the other at time ($t+\tau$). These signals are then multiplied and summations of all the transient components are performed. The auto-correlation function is described by the equations below.

For transient signals:

$$R_{aa}(\tau) = \int_{-\infty}^{\infty} a(t)a(t+\tau)dt \quad (6)$$

For stationary signals:

$$R_{aa}(\tau) = \text{Lim}_T \to \infty 1/T \int_{-T/2}^{+T/2} a(t)a(t+\tau)dt \quad (7)$$

Figure 6:
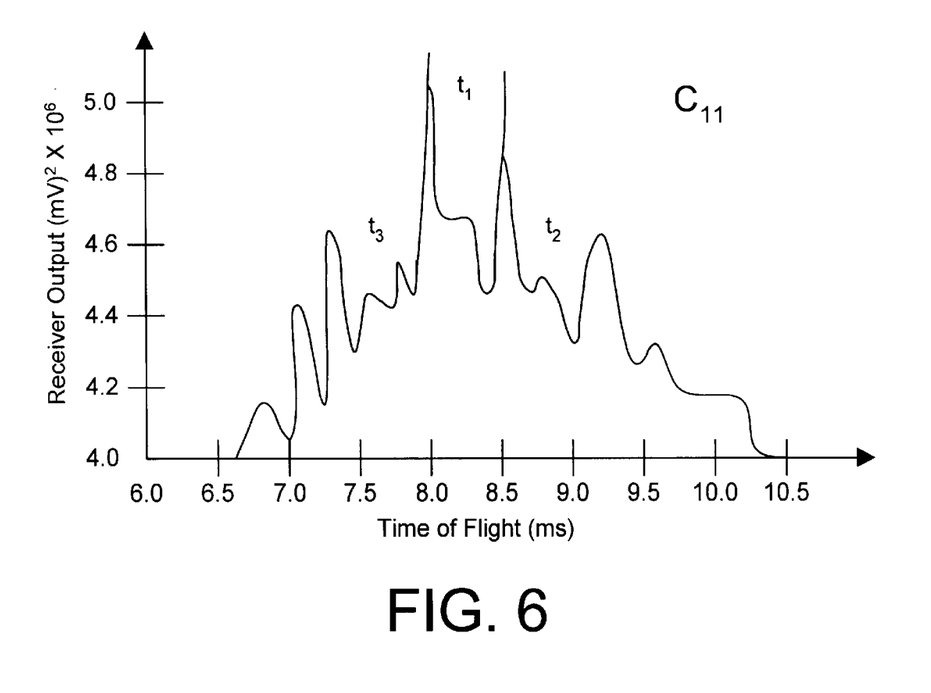
FIG. 6 is a graph showing the waveform of FIG. 5 after applying an auto-correlation function.

In equation (7), the spectrum periodicity is defined by T. The one condition for which the equation (7) is not applicable is when the noise level in the signal received by the receiver transducer is greater than the amplitude of the spectrum. Using equation (7), a rough estimate of the time of flight can be obtained, as shown by $t_1$ in the graph in FIG. 6. Ideally, $t_1$ should be equal to $t_2$ and $t_3$. As the graph in FIG. 6 shows, this is clearly not the case. For this reason, further processing is required by performing a cepstrum analysis 374 on the waveform of FIG. 6 to accurately determine the time of flight.

The waveform in FIG. 6 is subjected to power cepstrum $C_{aa}(t)$ according to the equation below.

$$C_{aa}(t) = F^{-1}\{\log S_{aa}(f)\} \quad (8)$$

where $F^{-1}$ is the inverse Fourier transform and $S_{aa}(f)$ is given as:

$$S_{aa}(f) = \Sigma |F\{a(t)\}|^2 \quad (9)$$

Figure 7:
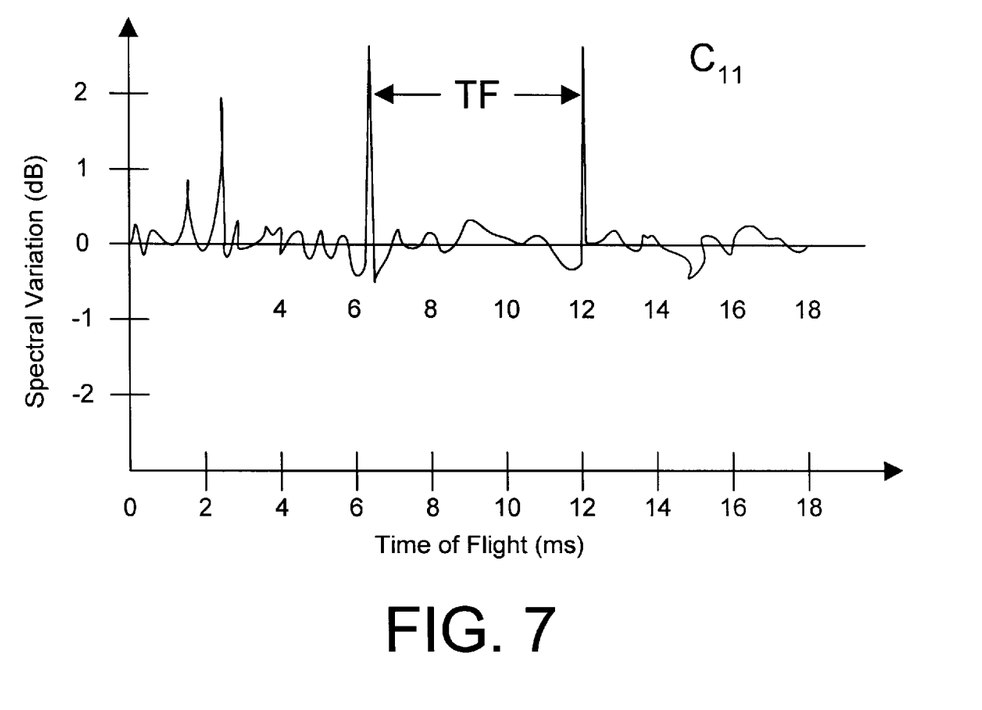
FIG. 7 is a graph showing the waveform of FIG. 6 after applying cepstrum analysis.

Equation 8 has the ability to detect periodic structures in the logarithmic spectrum, for example families of harmonics and/or side bands with uniform spacing. This helps in eliminating echoes and helps separate source and transmission path effects using convolution and deconvolution, respectively. The result of applying the cepstrum analysis to the waveform in FIG. 6 is the waveform in FIG. 7. The time of flight may be determined by the distance between two dominant peaks of approximately the same amplitude. We see from the waveform of FIG. 7 that the time of flight TF may be readily measured once the auto-correlation function and cepstrum analysis have been performed.

Once the time of flight measurements are made, velocity can be easily calculated by measuring board thickness. Assuming that the density of the sample under test is isotropic in nature and remains constant, longitudinal, transverse and off axes stiffness properties can be calculated using the following equations.

$$C_{11} = \rho v_{1/1}^2 \quad (10)$$

$$C_{22} = \rho v_{2/2}^2 \quad (11)$$

$$C_{33} = \rho v_{3/3}^2 \quad (12)$$

$$C_{12} = \rho v_{1/2}^2 \quad (13)$$

The wave speed propagating in a particular direction was determined by measuring the time period. The velocity $v_{i/j}$ is related to the thickness h and to the time of flight $t_{i/j}$ by the following equation.

$$V_{i/j} = h/t_{i/j} \quad (14)$$

In equation (14), $v_{i/j}$ corresponds to the velocity of the waves in the given direction.

In order to properly evaluate the properties determined using the apparatus and method of the preferred embodiments, experiments were conducted to find the effect of transducer and sampling frequencies on the velocity measurements. The experiments were conducted on an isotropic aluminum sample and on an anisotropic Nicalon/CAS-II composite sample. These samples were selected because the stiffness properties of these materials is well-documented, providing a standard by which we can measure the effectiveness of the method of the preferred embodiments. The effect of varying the frequency of the transmission transducer from 2 MHz to 5 MHz at a sampling frequency for the receiver transducer of 32 MHz is shown below in Table 2.

TABLE 2

| Material | Transducer Frequency (MHz) | Velocity (m/sec) |
| --- | --- | --- |
| Al | 2 | 6,526.1 |
| Al | 5 | 6,526.1 |
| Nicalon/CAS-II (anisotropic) | 2 | 7,516.4 |
| Nicalon/CAS-II (anisotropic) | 5 | 7,659.8 |

We see from the velocity values for aluminum that the measured velocity does not change when the transducer frequency changes from 2 MHz to 5 MHz. In addition, the velocity change when the transducer frequency changes from 2 MHz to 5 MHz for the anisotropic Nicalon/CAS-II sample changes less than two percent. This shows that varying the frequency of the transmitter transducer has very little effect on the accuracy of the test.

Next, the effect of changing the sampling rate of the receiver transducer was measured when the transmission transducer was excited at a frequency of 5 MHz. The results of these tests are shown below in Table 3.

TABLE 3

| Material | Sampling Frequency (MHz) | Velocity (m/sec) |
| --- | --- | --- |
| Al | 8 | 6,303.7 |
| Al | 16 | 6,364.2 |
| Al | 32 | 6,526.1 |

TABLE 3-continued

| Material | Sampling Frequency (MHz) | Velocity (m/sec) |
| --- | --- | --- |
| Al | 128 | 6,405.2 |
| Nicalon/CAS-II (anisotropic) | 8 | 7,444.5 |
| Nicalon/CAS-II (anisotropic) | 16 | 7,659.8 |
| Nicalon/CAS-II (anisotropic) | 32 | 7,659.8 |
| Nicalon/CAS-II (anisotropic) | 128 | 7,274.8 |

The total variation in velocity with sampling rate is less than six percent. These tests show that the effect of changing the sampling frequency are small and can be included in the velocity measurement variation.

Next, tests were then run using a 3 mm×3 mm sample of a 1.85 mm thick printed wiring board that consists of 22 layers of FR4 and copper. These samples were cut with a diamond wafering saw then polished with 0.05 micron alumina in an aqueous solution. Similar samples were prepared to perform tensile tests based on ASTM specification numbers D3552, E8, and D3039. The results from the tensile and ultrasonic tests are shown below in Table 4.

TABLE 4

| Material | $C_{11}$ (psi) Tensile Test | $C_{11}$ (psi) Method of the Invention |
| --- | --- | --- |
| Al 7075 | $1.04 \times 10^7$ (ASTM E8) | $0.99 \times 10^7$ |
| ABS 30–40% Glass Fiber | $1.19 \times 10^6$ (ASTM D3039) | $1.23 \times 10^6$ |
| Nicalon/CAS-II (anisotropic) | $20.37 \times 10^6$ (ASTM D3552) | $22.98 \times 10^6$ |
| 1.85 mm thick Printed Wiring Board | $2.4 \times 10^6$ (ASTM D3552) | $1.98 \times 10^6$ |

As the results in Table 4 show, the non-destructive test results that are obtained using the apparatus and method of the invention are within 5 to 17 percent of destructive tensile test results depending on the specific material being tested. These results establish that the signal processing technique of the preferred embodiments that uses a combination of an auto-correlation function with cepstrum analysis is an effective way of determining properties of an anisotropic sample under test.

The preferred embodiments thus disclose an apparatus and method for determining stiffness properties of an anisotropic sample under test, such as a multilayer printed wiring board, in a non-destructive manner. While the results vary from the results obtained from destructive testing, these results are close enough to allow determining within an acceptable tolerance level the stiffness of a multilayer printed circuit board without destroying the printed wiring board. This is a significant advancement in the art because costly printed wiring boards need not be destroyed to determine their stiffness properties.

One skilled in the art will appreciate that many variations are possible within the scope of the present invention. Thus, while the invention has been particularly shown and described with reference to preferred embodiments thereof, it will be understood by those skilled in the art that these and other changes in form and details may be made therein without departing from the spirit and scope of the invention. For example, one skilled in the art will recognize that other properties of a sample under test may be determined once the stiffness properties are known. For example, the Poisson's ratio of a sample under test may be readily computed once the Young's modulus and shear modulus are determined. The preferred embodiments expressly extend to the determination of any property of the sample under test using the apparatus and methods disclosed herein and their reasonable equivalents.

We claim:

1. An apparatus comprising:
   a transmitter transducer that generates an input waveform in a sample under test;
   a receiver transducer that receives the input waveform from the sample under test;
   an amplifier that amplifies the received input waveform to generate therefrom an amplified waveform;
   a digitizer that digitizes the amplified waveform to generate therefrom a digitized waveform;
   a digital signal processor that performs an auto-correlation function on the digitized waveform to produce a first resulting waveform and that performs a cepstrum analysis on the first resulting waveform to produce a second resulting waveform;
   a processing mechanism that determines time of flight from the second resulting waveform;
   a processing mechanism that determines velocity of the input waveform from the time of flight for the second resulting waveform; and
   a processing mechanism that determines from the velocity of the input waveform at least one property of the sample under test.

2. The apparatus of claim 1 wherein the at least one property includes the Young's modulus and the shear modulus for the sample under test.

3. The apparatus of claim 2 wherein the at least one property includes the Poisson's ratio for the sample under test.

4. The apparatus of claim 1 wherein the sample under test comprises a printed wiring board.

5. The apparatus of claim 1 wherein the sample under test comprises an anisotropic material.

6. An apparatus comprising:
   (1) a transmitter transducer that generates an input waveform having a frequency from 16 MHz to 120 MHz in a printed wiring board when placed in contact with the printed wiring board;
   (2) a receiver transducer that receives the input waveform from the printed wiring board when placed in contact with the printed wiring board in a position opposite to the position of the transmitter transducer;
   (3) a shear wave generator positioned adjacent to the receiver transducer that detects shear waves induced by the transmitter transducer;
   (4) an amplifier that amplifies the received input waveform to generate therefrom an amplified waveform;
   (5) a digitizer that digitizes the amplified waveform to generate therefrom a digitized waveform;
   (6) a digital signal processor that performs an auto-correlation function on the digitized waveform to produce a first resulting waveform and that performs a cepstrum analysis on the first resulting waveform to produce a second resulting waveform;
   (7) a processor coupled to the digital signal processor, the processor performing the steps of:
      (7A) determining time of flight from the second resulting waveform;
      (7B) determining velocity of the input waveform from the time of flight for the second resulting waveform; and
      (7C) determining from the velocity of the input waveform the Young's modulus and the shear modulus for the printed wiring board.

7. The apparatus of claim 6 wherein the processor further performs the step of:
   (7D) determining the Poisson's ratio for the sample under test.

8. A method for determining material properties of a sample under test, the method comprising the steps of:
   generating an input waveform in the sample under test;
   receiving the input waveform through the sample under test;
   amplifying the received input waveform and generating therefrom an amplified waveform;
   digitizing the amplified waveform to generate therefrom a digitized waveform;
   performing an auto-correlation function on the digitized waveform to produce a first resulting waveform;
   performing a cepstrum analysis on the first resulting waveform to produce a second resulting waveform;
   determining time of flight from the second resulting waveform;
   determining velocity of the input waveform from the time of flight for the second resulting waveform; and
   determining from the velocity of the input waveform at least one property of the sample under test.

9. The method of claim 8 wherein the at least one property includes the Young's modulus and the shear modulus for the sample under test.

10. The method of claim 9 wherein the at least one property includes the Poisson's ratio for the sample under test.

11. The method of claim 8 wherein the sample under test comprises a printed wiring board.

12. The method of claim 8 wherein the sample under test comprises an anisotropic material.

13. A method for determining material properties of a multilayer printed wiring board, the method comprising the steps of:
   (1) generating an input waveform having a frequency from 16 MHz to 120 MHz in a printed wiring board;
   (2) receiving the input waveform from the printed wiring board;
   (3) detecting shear waves induced by input waveform;
   (4) amplifying the received input waveform to generate therefrom an amplified waveform;
   (5) digitizing the amplified waveform to generate therefrom a digitized waveform;
   (6) performing an auto-correlation function on the digitized waveform to produce a first resulting waveform;
   (7) performing a cepstrum analysis on the first resulting waveform to produce a second resulting waveform;
   (8) determining time of flight from the second resulting waveform;
   (9) determining velocity of the input waveform from the time of flight for the second resulting waveform; and
   (10) determining from the velocity of the input waveform the Young's modulus and the shear modulus for the printed wiring board.

14. The method of claim 13 further comprising the step of determining the Poisson's ratio for the sample under test.

* * * * *